United States Patent
Maida, Jr. et al.

(10) Patent No.: US 11,353,422 B2
(45) Date of Patent: Jun. 7, 2022

(54) IN SITU TREATMENT OF CHEMICAL SENSORS

(71) Applicant: Halliburton Energy Services, Inc., Houston, TX (US)

(72) Inventors: John Laureto Maida, Jr., Houston, TX (US); Michel Joseph Leblanc, Houston, TX (US); Neal Gregory Skinner, Lewisville, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 713 days.

(21) Appl. No.: 16/331,886

(22) PCT Filed: Oct. 14, 2016

(86) PCT No.: PCT/US2016/056974
§ 371 (c)(1),
(2) Date: Mar. 8, 2019

(87) PCT Pub. No.: WO2018/071036
PCT Pub. Date: Apr. 19, 2018

(65) Prior Publication Data
US 2019/0227029 A1    Jul. 25, 2019

(51) Int. Cl.
*G01N 27/416* (2006.01)
*E21B 49/08* (2006.01)
*G01N 33/00* (2006.01)

(52) U.S. Cl.
CPC ....... *G01N 27/4163* (2013.01); *E21B 49/087* (2013.01); *G01N 33/0031* (2013.01); *G01N 33/0044* (2013.01)

(58) Field of Classification Search
CPC .......... G01N 27/4163; G01N 33/0031; G01N 33/0044; E21B 49/087
See application file for complete search history.

(56) References Cited

U.S. PATENT DOCUMENTS

| | | | |
|---|---|---|---|
| 7,318,343 | B2 | 1/2008 | Coenen |
| 8,090,227 | B2 | 1/2012 | Skinner |
| 2004/0244971 | A1 | 12/2004 | Shammai et al. |
| 2010/0126731 | A1 | 5/2010 | Vasques et al. |
| 2014/0352397 | A1 | 12/2014 | Smits |

FOREIGN PATENT DOCUMENTS

| | | | |
|---|---|---|---|
| WO | 9857030 | 12/1998 | |
| WO | WO-2015094194 A1 * | 6/2015 | ............. E21B 41/00 |

OTHER PUBLICATIONS

ISRWO International Search Report and Written Opinion for PCT/US2016/048458 dated Jun. 27, 2017.
Halliburton Energy Services, Inc. "Casing Equipment", Halliburton Catalog, 2015.
https://www.theleeco.com/products/precision-microhydraulics/check-valves/ (The Lee Company).

* cited by examiner

*Primary Examiner* — Christopher Adam Hixson
(74) *Attorney, Agent, or Firm* — Thomas Rooney; C. Tumey Law Group PLLC

(57) ABSTRACT

Systems and methods for a treatment of chemical sensors placed in a wellbore. A method may comprise providing a chemical sensor disposed in a sensing chamber, wherein the chemical sensor is on an optical fiber installed in a wellbore; optically interrogating the chemical sensor with the optical fiber; and pumping a treatment fluid through a fluid supply line and into the sensing chamber.

20 Claims, 5 Drawing Sheets

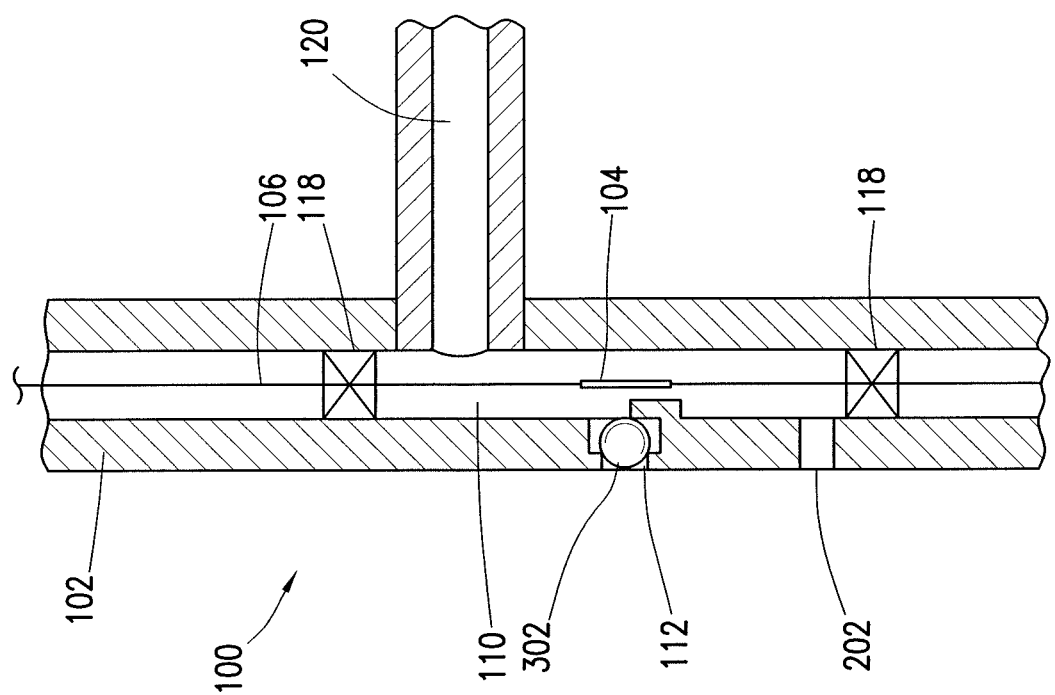
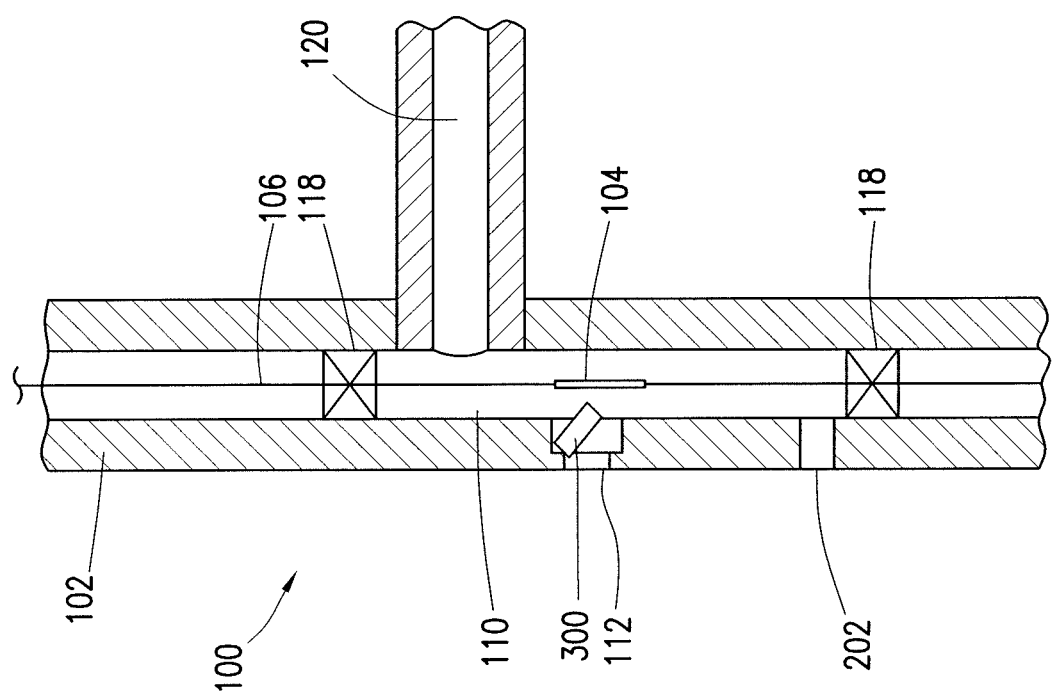

IN SITU TREATMENT OF CHEMICAL SENSORS

BACKGROUND

Chemical sensors may be installed in a wellbore to determine properties of downhole fluids, including composition, concentration, and partial pressure, among others. Chemical sensors may be integrally or otherwise connected to an optical waveguide. A string of chemical sensors may be installed in the wellbore to provide information at various locations. In the wellbore, chemical sensors may degrade over time for various reasons and may require continuous or periodic recalibration and/or refreshing of constituent analytical reagents along a chemical sensor string. Periodic recalibration of these chemical sensors may be necessary due to their exposure to high temperature corrosive aqueous fluids found in both flowing and stagnant cavities along a wellbore.

Additionally, deposits may form on or around the chemical sensors due to their contact with various heavy hydrocarbons and/or other fluids commonly present downhole. These deposits may form layers on top of the sensor element. Such deposits may cause a slower response for the chemical sensors or may cause them to have an incorrect reading.

BRIEF DESCRIPTION OF THE DRAWINGS

These drawings illustrate certain aspects of some examples of the present disclosure, and should not be used to limit or define the disclosure.

FIG. 3A is a schematic illustration of an example of a sensing chamber with a flapper check valve.

FIG. 3B is a schematic illustration of an example of a sensing chamber with a ball check valve.

DETAILED DESCRIPTION

Figure 1A:
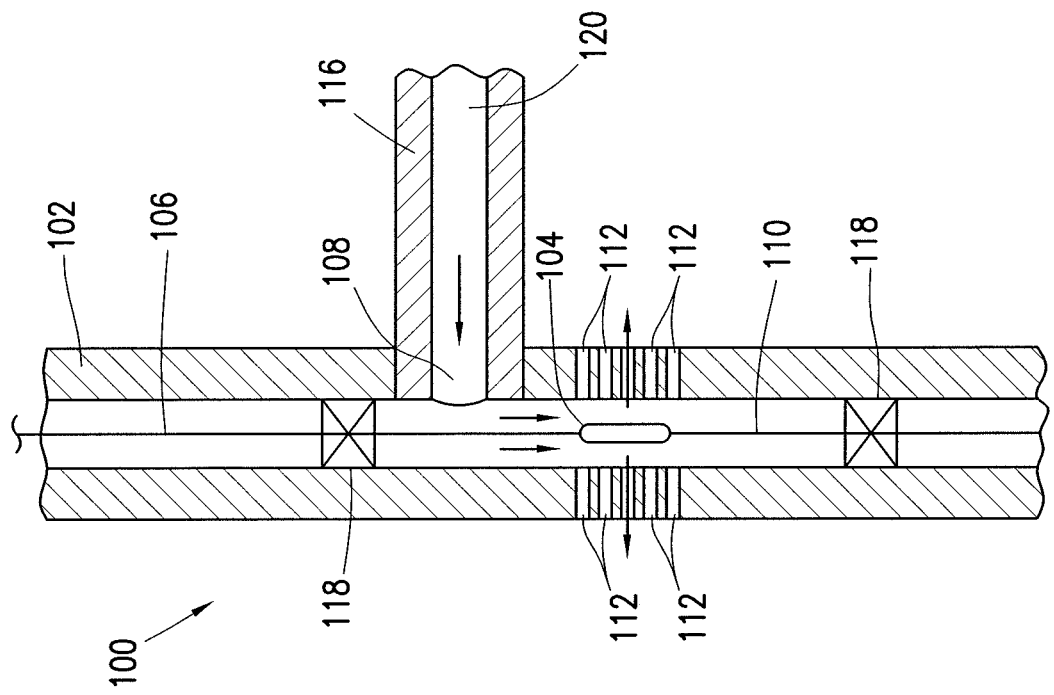
FIG. 1A is a schematic illustration of an example of a chemical sensor disposed in a wellbore.

This disclosure may generally relate to treatment of chemical sensors placed in a wellbore. This treatment may include, without limitation, a periodic cleaning, replenishing, calibrating and/or refreshing of the chemical sensors. Systems and methods disclosed herein may include a wellbore circulatory system for conveyance and delivery of a treatment fluid to the chemical sensors, for example, to clean, replace and/or rejuvenate existing in-well reagents for improving analyte measurement accuracy and sensor sensitivity. A fluid supply line may be disposed alongside a string of chemical sensors (e.g., optical and/or electrical) to hydraulically deliver the treatment fluid. The treatment fluid may be delivered either continuously or as required (on demand). The fluid supply line may be sealed when unused to prevent leakage to the surface. Additionally, the fluid supply line may also contain optical fibers and/or electrical conductors which may be employed to optically and/or electronically interrogate the chemical sensors.

The treatment fluid may comprise any of a variety of different components to clean, replenish, calibrate and/or refresh the chemical sensors. By way of example, the treatment fluid may comprise a rejuvenation agent. The rejuvenation agent may comprise a new chemical reagent to replenish and/or refresh the in-well reagents of the chemical sensors. Examples of suitable rejuvenation agents may comprise fresh water, pH buffer solution, a solution with a known ionic concentration, or combinations thereof. By way of further example, the treatment fluid may comprise a cleaning agent for the removal of deposits from the chemical sensors. Examples of suitable cleaning agents may comprise hydrocarbon solvent (e.g., ethylene), acid, a surfactant in a water-based solution or combinations thereof. Those of ordinary skill in the art, with the benefit of this disclosure should be able to select an appropriate treatment fluid to treat the chemical sensor, depending on a number of factors, including the type of chemical sensor and treatment purpose, among others.

A sensing system may comprise an optical waveguide disposed in a wellbore, wherein the optical waveguide comprises a chemical sensor; a conduit assembly disposed in the wellbore, wherein the optical waveguide is disposed in the conduit assembly, wherein the conduit assembly comprises a sensing chamber that contains the chemical sensor; and a fluid supply line disposed in the wellbore and coupled to the sensing chamber. The sending system may further comprise any of the following elements in any combination. For example, the sensing system may further comprise a surface-based circulatory fluid pump coupled to the fluid supply. The chemical sensor may be an optical sensor. The sensing system may further comprise a check valve positioned to control flow of a sensed fluid to the sensing chamber. The check valve may be a flapper valve, ball valve or an elastomeric valve. The sensing system may further comprise a treatment fluid, wherein the treatment fluid is disposed in the fluid supply conduit. The sensing system may further comprise a supply check valve positioned in the fluid supply line to control flow of a treatment fluid into the sensing chamber. The sensing chambers may be monitored remotely by distributed acoustic sensing. The optical fiber may be hydraulically sealed at a top and a bottom of the sensing chamber. The sensing chamber may comprise at least one aperture for entry of a sensed fluid, an inlet at one end fluidly coupled to the fluid supply line, and a port at an opposite end from the inlet for exit of a treatment fluid from the fluid supply line. The sensing system may further comprise an array of chemical sensors disposed along the optical waveguide in sensing chambers, wherein the fluid supply line may be fluidly coupled to the sensing chambers.

A method may comprise providing a chemical sensor disposed in a sensing chamber, wherein the chemical sensor is on an optical fiber installed in a wellbore; optically interrogating the chemical sensor with the optical fiber; and pumping a treatment fluid through a fluid supply line and into the sensing chamber. The method may further comprise any of the following elements in any combination. For example, the chemical sensors may be in contact with a downhole fluid during the step of optically interrogating. The treatment fluid may be pumped to the sensing chamber through one or more supply check valves, and wherein one or more check valves in the sensing chamber may be closed by the pressure of the treatment fluid. The treatment fluid may comprise fresh water, a pH buffer solution or any combination thereof. The treatment fluid may comprise a hydrocarbon solvent, ethylene, acid, surfactants in a water-based solution or any combination thereof. The treatment fluid may remove deposits from the chemical sensors. The treatment fluid may purge a downhole fluid from the sensing chamber. The treatment fluid may have a known concentration of the analyte and may be used for calibration of one of more chemical sensors. Two or more treatment fluids may be used in sequence in order to permit the calibration of one or more chemical sensors.

FIG. 1A illustrates a downhole sensing system 100. As illustrated, downhole sensing system 100 may include conduit assembly 102, chemical sensor 104, and optical waveguide 106. Without limitation, conduit assembly 102 may be any conduit assembly 102 for installing chemical sensor 104 and optical waveguide 106 in a wellbore. By way of assembly, conduit assembly 102 may comprise a metal tube or cable. While not shown on FIG. 1A, the conduit assembly 102 may be installed in a wellbore on a production tubing string, casing string, or other suitable wellbore conduit. The conduit assembly 102 may be installed on the interior or the exterior of the tubing string. Alternatively, the conduit assembly 102 and/or the chemical sensor 104 may be integrally formed with the wellbore conduit, such as a tubing string. Any suitable means may be used for attachment of the conduit assembly 102 to the wellbore conduit, including without limitation, clamps. Alternatively, the conduit assembly 102 and chemical sensor 104 may be installed in a wellbore without attachment to a wellbore conduit, such as a tubing string.

As illustrated, conduit assembly 102 may include chemical sensor 104 which may be disposed along optical waveguide 106. Alternatively, conduit assembly 102 may include an array of chemical sensors 104 (not shown), for example, disposed along the optical waveguide. Without limitation, optical waveguide 106 may include, for example, any type of optical fiber, including without limitation a fiber optic cable. As illustrated, optical waveguide 106 may be disposed in conduit assembly 102. While not shown, multiple optical waveguides 106 may be disposed in conduit assembly 102. The optical waveguide 106 may be communicatively attached to surface equipment (not shown) which may include a motorized reel, or other suitable equipment, to raise and lower the conduit assembly 102 into and out of a wellbore (if temporarily installed). Surface equipment may include an information handling system (not shown) for receiving signals from chemical sensor 104.

Chemical sensor 104 may include any of a variety of chemical sensors that may be used in wellbore operations. Without limitation, chemical sensor 104 may be used to sense various properties of downhole fluids, such as formation fluids, fluids introduced from the surface, or combinations thereof. For example, the chemical sensor 104 may be operable to determine properties of downhole fluids, including composition, concentration, and partial pressure, among others. By way of example, chemical sensor 104 may determine a concentration of a target analyte dissolved in a downhole fluid (e.g., the concentration of potassium ion K+). Target analytes may include pH, the concentrations of various ions such as Ca, K, Na, P, etc., water, natural gas (methane), oil, mud, $H_2$, JLM, $H_2S$, boron, iron oxide, simple inorganic salts, etc. As illustrated, conduit assembly 102 may include a sensing chamber 110 in which chemical sensor 104 may be disposed. Sensing chamber 110 may include apertures 112 that may allow downhole fluids to readily circulate through the sensing chamber 110. Alternatively, conduit assembly 102 may include a plurality of sensing chambers 110 (not shown), for example, where there may be an array of chemical sensors 104. The apertures 112 may allow the sensed fluid 114 (e.g., downhole fluid) to move in and out of sensing chamber 110 to contact chemical sensor 104. Chemical sensor 104 may sense one or more properties of sensed fluid 114 and communicate this information the surface via optical waveguide 106, for example. As will be discussed in more detail below with respect to FIG. 1B, sensing chamber 110 may further include a fluid inlet 108, which may be coupled to fluid supply line 116. Accordingly, sensing chamber 110 may be in communication with sensed fluid 114 and with fluid supply line 116. However, a check valve may be disposed in fluid supply line 116, for example, with a cracking pressure sufficiently large to prevent treatment fluid from entering sensing chamber 110 during operation of chemical sensor 104. While not shown, optical waveguides and/or electrical conductors may be deployed in the fluid supply line 116, for example, to interrogate, the chemical sensor 104.

Without limitation, the optical waveguide 106 running from above and to below the chemical sensor 104 may be hydraulically sealed at the top and bottom of the sensing chamber 110 with seals 118. These seals 118 may hydraulically isolate the individual sensing chamber 110 along optical waveguide 106. Seals 118 may include any suitable type of seal for use with optical waveguide 106, including fiber seals, such as hermetic fiber seals.

Figure 1B:
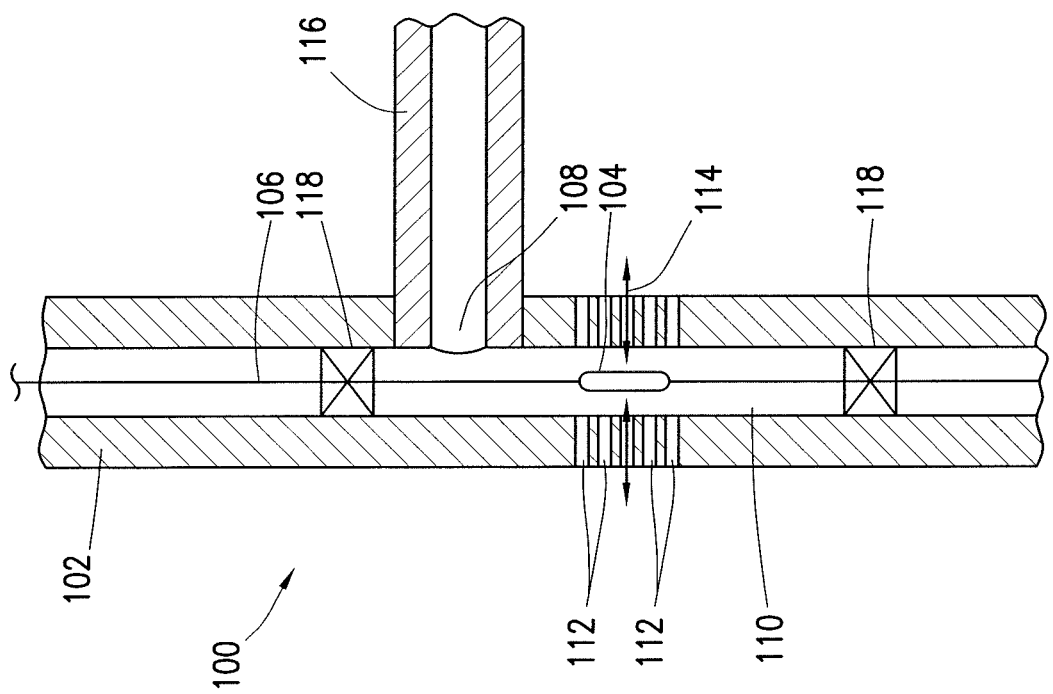
FIG. 1B is a schematic illustration of an example of fluid flow from a fluid supply line disposed in the wellbore.

FIG. 1B illustrates an example of contacting chemical sensor 104 with a treatment fluid 120 (e.g., purge, cleaning, and/or replenishment fluid) from a fluid supply line 116. As desired, a treatment fluid 120 may be delivered from the surface to sensing chamber 110. Treatment fluid 120 may travel from surface, through fluid supply 116, and into sensing chamber 110 by way of fluid inlet 108. In sensing chamber 110, treatment fluid 120 may contact chemical sensor 104. As previously described, treatment fluid 120 may comprise any of a variety of different components to clean, replenish, and/or refresh the chemical sensor 104. As illustrated, treatment fluid 120 may exit sensing chamber 110 by way of apertures 112. As will be discussed below with respect to FIGS. 2A and 2B, treatment fluid 120 may alternatively exit sensing chamber 110 by way of another opening formed in sensing chamber (e.g., port 202 shown on FIG. 2B). After exiting the sensing chamber 110, the treatment fluid 120 may be returned to surface, for example, by way of a return line which may be coupled to sensing chamber 110, or the treatment fluid 120 may be discharged into the wellbore.

Figure 2A:
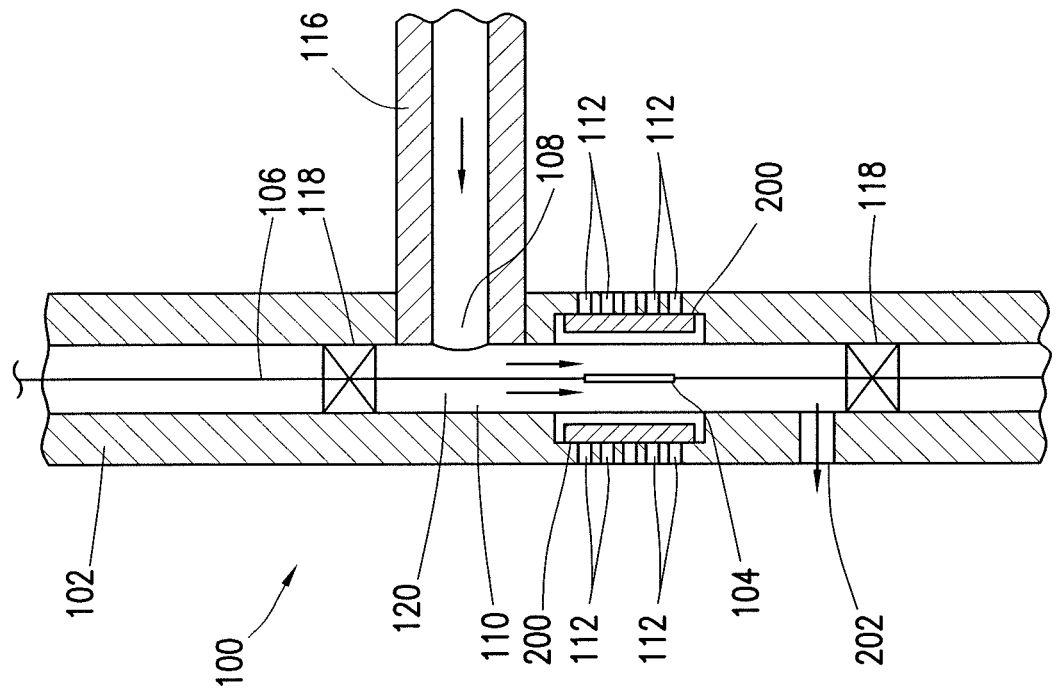
FIG. 2A is a schematic illustration of an example of an open elastomeric check valve in the sensing chamber.
Figure 2B:
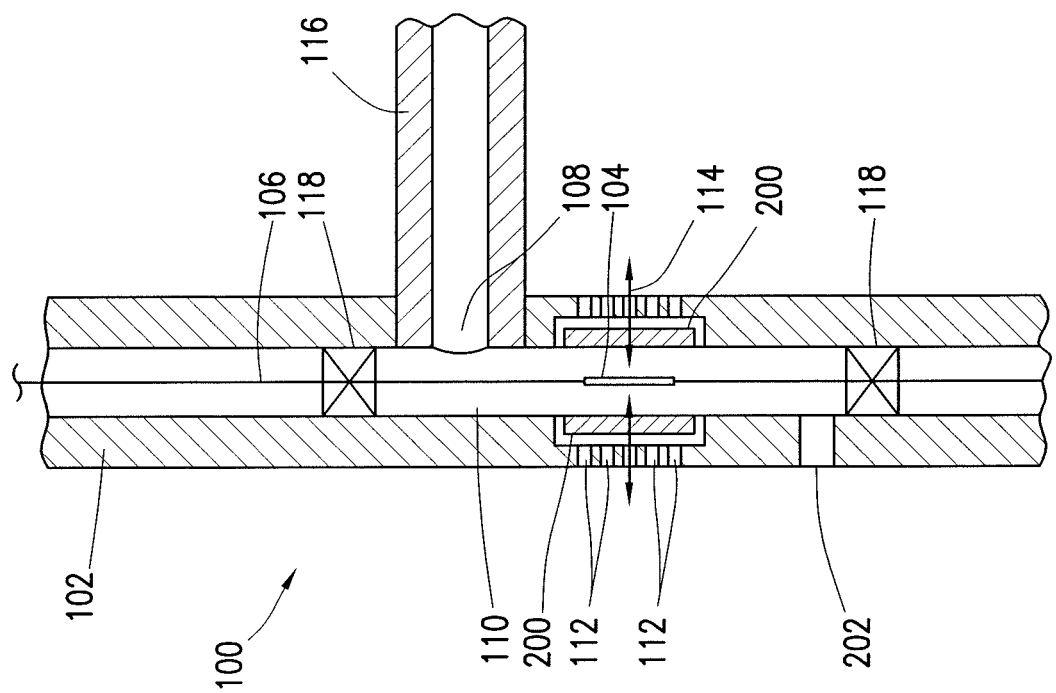
FIG. 2B is a schematic illustration of an example of a closed elastomeric check valve in the sensing chamber.

FIGS. 2A and 2B illustrate using an example of downhole sensing system that uses a check valve 200 in the sensing chamber 110. As illustrated, check valve 200 may be disposed over apertures 112, for example, to allow sensed fluid 114 into sensing chamber 110 in an open configuration (FIG. 2A) or prevent passage of sensed fluid 114 through apertures 112 in a closed configuration (FIG. 2B). FIG. 2A illustrates a sensing configuration using a check valve 200 in an open position which may allow sensed fluid 114 to move in and out of sensor 104. Any suitable check valve 200 may be used, including without limitation an elastomeric check valve as shown in FIGS. 2A and 2B. Pressure differential between the interior and exterior of sensing chamber 110 may be used to open/close check valve 200. FIG. 2B illustrates a treatment configuration in which treatment fluid 120 may be introduced to sensing chamber 110 by way of fluid supply line 116. As illustrated, check valve 200 may close due to pressure of the treatment fluid 120. The closure of check valve 200 may prevent sensed fluids 114 from reaching chemical sensor 104. As illustrated, sensing chamber 110 may further include a port 202. Treatment fluid 120 may exit sensing chamber 110 by way of port 202. Port 202 may be positioned on an opposite end of sensing chamber 110 from fluid inlet 108. When check valve 200 is in a closed position, the treatment fluid 120 may be forced to travel past the chemical sensor 104 exiting through port 202. Without limitation, port 202 may be positioned to force treatment fluid 120 through the entire length of the sensing chamber 110 and along the entire length of the chemical sensor 104. After exiting the sensing chamber 110, the treatment fluid 120 may be returned to surface, for example, by way of a return line which may be coupled to sensing chamber 110, or the treatment fluid 120 may be discharged into the wellbore.

FIGS. 3A and 3B illustrate alternative types of check valves 200 that may be used in sensing chamber 110, for example, a flapper style check valve 300 (shown in FIG. 3A) or ball check valve 302 (shown in FIG. 3B) may be used to close the aperture 112 in the sensing chamber 110 to force the treatment fluid 120 (e.g., FIGS. 2A & 2B) through the sensing chamber 110.

Figure 4:
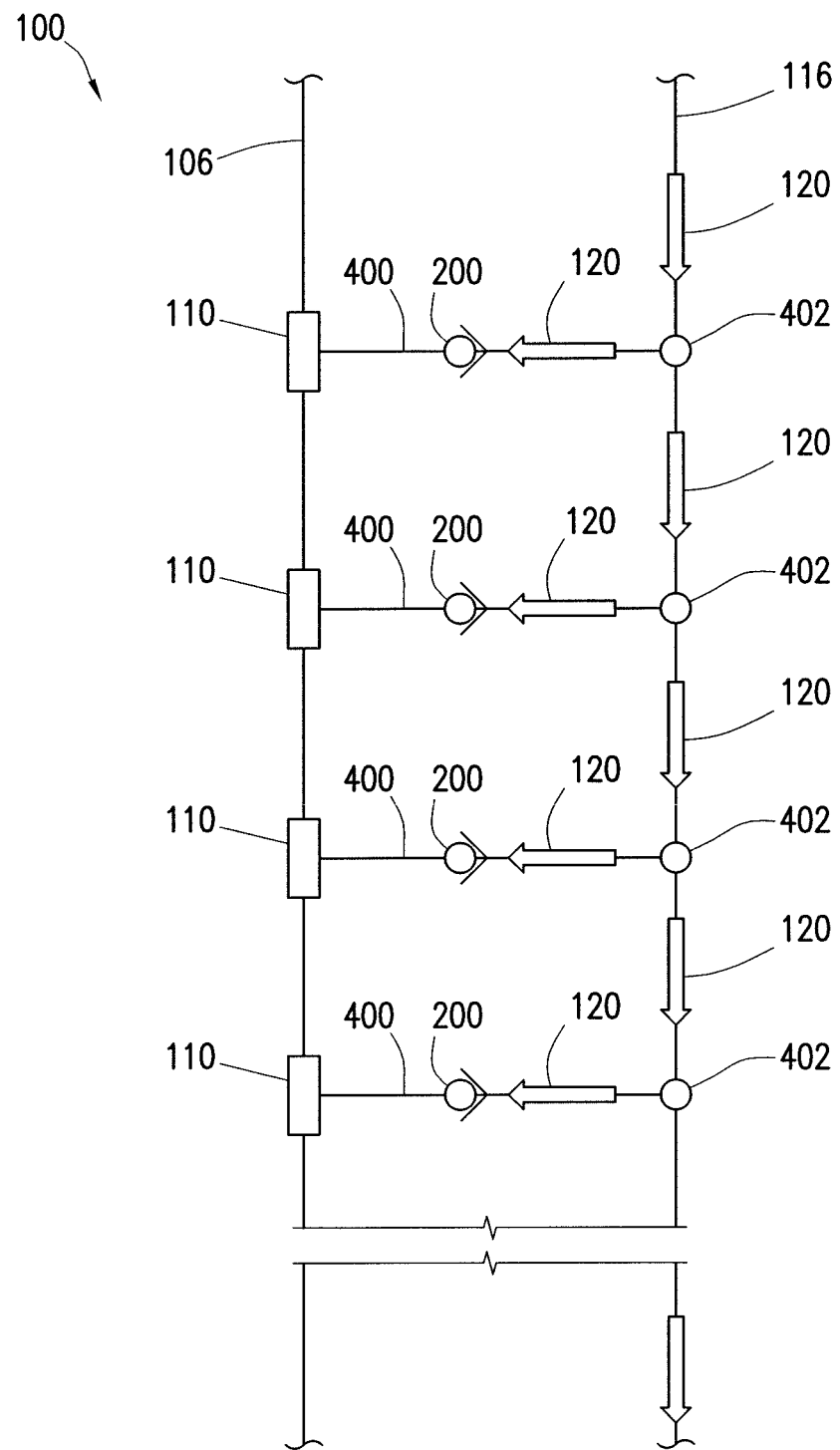
FIG. 4 is a schematic illustration of an example of a fluid supply line connected to sensing chambers arrayed along the optical waveguide.

FIG. 4 illustrates a sensing system 100 that comprises an array of sensing chambers 110. As illustrated, the array of sensing chambers 110 may be arranged on optical waveguide 106. By way of example, the sensing chambers 110 may be longitudinally spaced on optical waveguide 106. Without limitation, the sensing chambers 110 may be fluidly connected to fluid supply line 116 to deliver the pumping fluid 120 to the sensing chambers 110. While FIG. 4 illustrates fluid supply line 116 arranged in parallel with optical waveguide 106, it should be understood that the fluid supply line 116 and optical waveguide 106 do not necessarily need to be in a parallel configuration. The fluid supply line 116 may be a conventional control line with junctions 402 fluidly connecting the individual sensing chambers 110 through supply check valves 200 and inlet lines 400. As illustrated, the supply check valves 200 may be disposed inline in the inlet lines 400. The supply check valves 200 may be pressure activated, for example, so that fluid flow up to the surface from sensing chambers 110 may be prevented, while allow fluid flow from the surface to and around the chemical sensors 104 (e.g., FIGS. 1A and 1B) disposed in sensing chambers 110. The desired treatment fluid 120 may be pumped down the fluid supply line 116 from the surface (not shown), through the supply check valves 200 and inlet lines 400 to the individual sensing chambers 110. Distributed acoustic sensing (DAS) may be used with one fiber in the optical waveguide 106 to determine that all the individual sensing chambers 110 receive the proper flow rate from the fluid supply line 116. In this way, the proper operation of the sensing system 100 including sensing chambers 110 may be monitored remotely. FIG. 4 illustrates one fluid delivery line (e.g., fluid supply line 116) connected to all of the sensing chambers 110 arrayed along the optical waveguide. However, not all chemical sensors 104 may require the same treatment fluid 120. For this reason, several fluid supply lines (not shown) may be positioned downhole (e.g., run in parallel) along the array of sensing chambers 110 selectively connecting each chemical sensor 104 to the line carrying the proper fluid for each sensor 104.

Figure 5:
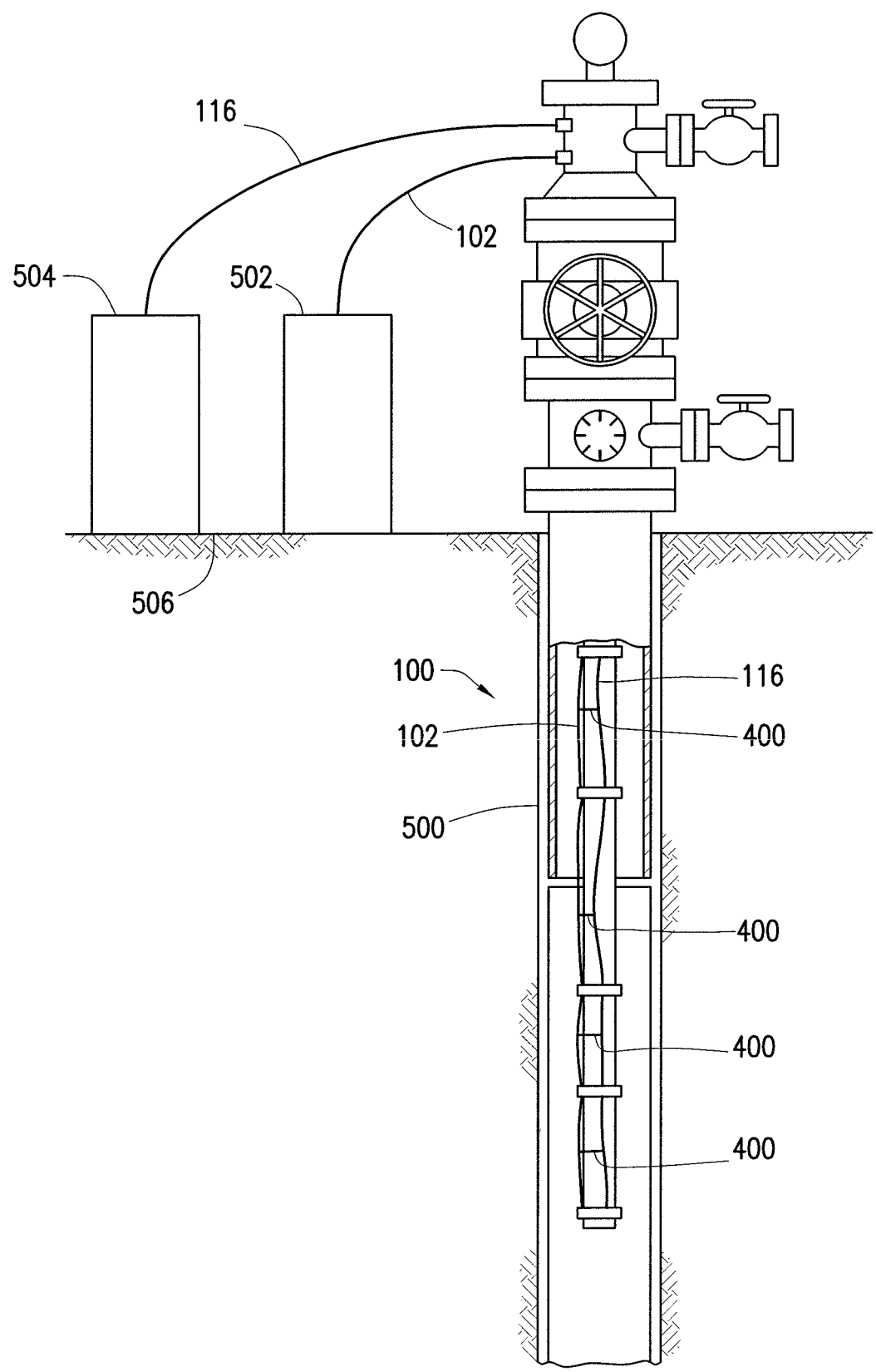
FIG. 5 is a schematic illustration of an example of a sensing system positioned in a wellbore.

FIG. 5 illustrates sensing system 100 positioned in wellbore 500. Signal generator/detector 502 may be optically coupled to optical wave guide 106 (shown in FIGS. 1A and 1B) within conduit assembly 102. Fluid supply line 116 may be fluidly coupled to pump 504 which may be positioned on the surface 506. The signal generator/detector 502 may responsively produce electrical measurements of a backscattered light phase shift at chemical sensors 104 (shown on FIGS. 1A and 1B). Signal generator/detector 502 may be controlled by a computer system. The pump 504 may be a positive displacement pump or a centrifugal pump. Pump 504 may pump a treatment fluid into fluid supply line 116.

Referring to FIGS. 1A and 5, pump 504 can be used to pump a sequence of treatment fluids 120 of known but different concentrations of the analyte so as to permit a calibration from the readings made from signal generator/detector 502 for a concentration value used.

Systems and methods disclosed herein may extend the life of chemical sensors 104 and may be compatible with existing downhole completions, tools and operations. By way of example, systems and methods may allow treatment of chemical sensors 104 in the wellbore. Also, systems and methods disclosed herein may relieve the need for well intervention, for example, to clean/remediate the chemical sensors.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A sensing system comprising:
   an optical waveguide disposed in a wellbore, wherein the optical waveguide comprises a chemical sensor;
   a conduit assembly disposed in the wellbore, wherein the optical waveguide is disposed in the conduit assembly, wherein the conduit assembly comprises a sensing chamber that contains the chemical sensor; and
   a fluid supply line disposed in the wellbore and coupled to the sensing chamber.

2. The sensing system of claim 1, further comprising a surface-based circulatory fluid pump coupled to the fluid supply.

3. The sensing system of claim 1, wherein the chemical sensor is an optical sensor.

4. The sensing system of claim 1, further comprising a check valve positioned to control flow of a sensed fluid to the sensing chamber.

5. The sensing system of claim 4, wherein the check valve is a flapper valve, ball valve or an elastomeric valve.

6. The sensing system of claim 1, further comprising a treatment fluid, wherein the treatment fluid is disposed in the fluid supply conduit.

7. The sensing system of claim 6, further comprising a supply check valve positioned in the fluid supply line to control flow of a treatment fluid into the sensing chamber.

8. The sensing system of claim 1, wherein the sensing chambers are monitored remotely by distributed acoustic sensing.

9. The sensing system of claim 1, wherein the optical fiber is hydraulically sealed at a top and a bottom of the sensing chamber.

10. The sensing system of claim 1, wherein the sensing chamber comprise at least one aperture for entry of a sensed fluid, an inlet at one end fluidly coupled to the fluid supply line, and a port at an opposite end from the inlet for exit of a treatment fluid from the fluid supply line.

11. The sensing system of claim 1, further comprising an array of chemical sensors disposed along the optical waveguide in sensing chambers, wherein the fluid supply line is fluidly coupled to the sensing chambers.

12. A method comprising:
   providing a chemical sensor disposed in a sensing chamber, wherein the chemical sensor is on an optical fiber installed in a wellbore;
   optically interrogating the chemical sensor with the optical fiber; and
   pumping a treatment fluid through a fluid supply line and into the sensing chamber.

13. The method of claim 12, wherein the chemical sensors are in contact with a downhole fluid during the step of optically interrogating.

14. The method of claim 12, wherein the treatment fluid is pumped to the sensing chamber through one or more supply check valves, and wherein one or more check valves in the sensing chamber are closed by the pressure of the treatment fluid.

15. The method of claim 12, wherein the treatment fluid comprises fresh water, a pH buffer solution or any combination thereof.

16. The method of claim 12, wherein the treatment fluid comprises a hydrocarbon solvent, ethylene, acid, surfactants in a water-based solution or any combination thereof.

17. The method of claim 12, wherein the treatment fluid removes deposits from the chemical sensors.

18. The method of claim 12, wherein the treatment fluid purges a downhole fluid from the sensing chamber.

19. The method of claim 12, wherein the treatment fluid has a known concentration of the analyte and is used for calibration of one of more chemical sensors.

20. The method of claim 12, wherein two or more treatment fluids are used in sequence in order to permit the calibration of one or more chemical sensors.

* * * * *